US012144900B2

(12) United States Patent
Alva et al.

(10) Patent No.: US 12,144,900 B2
(45) Date of Patent: Nov. 19, 2024

(54) METHODS AND DEVICES FOR STERILIZING ORGANIC PRODUCTS

(71) Applicants: Junia Suresh Alva, Mumbai (IN); Vernon Rainer Alva, Mumbai (IN)

(72) Inventors: Junia Suresh Alva, Mumbai (IN); Vernon Rainer Alva, Mumbai (IN)

( * ) Notice: Subject to any disclaimer, the term of this patent is extended or adjusted under 35 U.S.C. 154(b) by 757 days.

(21) Appl. No.: 17/423,881

(22) PCT Filed: Feb. 5, 2019

(86) PCT No.: PCT/IN2019/050085
§ 371 (c)(1),
(2) Date: Jul. 18, 2021

(87) PCT Pub. No.: WO2020/152694
PCT Pub. Date: Jul. 30, 2020

(65) Prior Publication Data
US 2022/0125965 A1    Apr. 28, 2022

(30) Foreign Application Priority Data
Jan. 22, 2019  (IN) .............................. 201921002694

(51) Int. Cl.
*A61L 2/00*  (2006.01)
*A61L 2/20*  (2006.01)
(Continued)

(52) U.S. Cl.
CPC ........... *A61L 2/0094* (2013.01); *A61L 2/0047* (2013.01); *A61L 2/202* (2013.01); *A61L 2/24* (2013.01);
(Continued)

(58) Field of Classification Search
CPC ..................................... A61L 2/00; A61L 2/24
(Continued)

(56) References Cited

U.S. PATENT DOCUMENTS 2,701,205 A    2/1955  Ekelund et al.
6,255,103 B1 * 7/2001  Tamaoki ................ C12M 37/00
                                                                236/3
(Continued)

FOREIGN PATENT DOCUMENTS

EP    0755190 A1    1/1997
EP    1785149 A1    3/2008

OTHER PUBLICATIONS

International Search Report and Written Opinion received for PCT Patent Application No. PCT/IN2019/050085, dated Jul. 2, 2019, 09 pages.

*Primary Examiner* — Monzer R Chorbaji
(74) *Attorney, Agent, or Firm* — Scott D. Swanson; Shaver Swanson

(57) ABSTRACT

The invention relates to sterilizing one or more samples of an organic product placed in a chamber of a sterilization device. The method includes, introducing a specified quantity of a gaseous composition comprising a predefined proportion of ozone and carbon monoxide through at least one inlet of the chamber. The method includes, subjecting each sample with ultraviolet light and the gaseous composition for predefined time period in a controlled atmosphere maintained at 90-100% humidity level and a temperature of −10 to 5 degree Celsius within the chamber. The method includes releasing the gaseous composition through at least one outlet from the chamber upon completion of the predefined time period, while simultaneously introducing purified air into chamber through the at least one inlet, until presence of the gaseous composition in the atmosphere of the chamber reaches below a threshold value.

15 Claims, 7 Drawing Sheets

(51) Int. Cl.
*A61L 2/24* (2006.01)
*B01J 19/08* (2006.01)
*G01N 23/00* (2006.01)

(52) U.S. Cl.
CPC ..... *A61L 2202/122* (2013.01); *A61L 2202/14* (2013.01); *A61L 2202/22* (2013.01)

(58) Field of Classification Search
USPC .................. 422/22, 24, 28, 186, 186.3, 292; 250/455.11
See application file for complete search history.

(56) References Cited

U.S. PATENT DOCUMENTS

| | | |
|---|---|---|
| 2004/0052702 A1 | 3/2004 | Shuman et al. |
| 2006/0008400 A1 | 1/2006 | Gutman |
| 2009/0081075 A1* | 3/2009 | Hashiba .................... A61L 2/24 |
| | | 422/186 |

* cited by examiner

METHODS AND DEVICES FOR STERILIZING ORGANIC PRODUCTS

CROSS-REFERENCE TO RELATED APPLICATION

The instant application is related to granted Indian Patent No: 335463, titled, "METHODS AND APPARATUSES FOR STERILIZING ORGANIC PRODUCTS" and co-pending PCT Application No. PCT/IN/2019050085, inventors Junia Suresh Alva and Vernon Rainer Alva, Filed: On 22 Jan. 2019 which is incorporated in its entirety herewith.

FIELD OF THE INVENTION

The present invention relates generally to preservation of organic products. More particularly the present invention relates to methods and devices for sterilizing organic products.

BACKGROUND OF THE INVENTION

Preservation of organic products, such as fruits, vegetables, meat, fish, poultry, blood plasma and other biodegradable products, involves delaying an onset of spoilage. As spoilage is caused primarily due to microbial overgrowth, preservation includes various techniques that prevent and/or retard microbial growth in the organic products. Various sterilization or disinfecting methods exist in practice for preventing and/or retarding microbial growth in the organic products. Sterilizing organic products, results in prolonged shelf life, and thereby reduction in economic losses to industries (e.g. food processing industries) dealing with processing of organic products.

An existing technique of sterilization includes use of heat for specified time periods to kill microbes existing in organic products. While use of heat does kill several pathogens thriving in the organic products, it results in breakdown of molecular structures of the organic food products. Such breakdown of molecular structures is unfavorable especially in food products such as meat and fish.

Another technique of sterilization includes immersing organic products in various chemical agents such as chlorine, hydrogen peroxide and other disinfecting solutions for inhibiting microbial growth. Usually, chemical agents are used in an aqueous form, during the sterilization process. Such aqueous agents result in unwanted water retention in the organic products during sterilization. Excess water not only makes the product spongy but also creates a ground for further bacterial growth. Further excess water retention may result in adulteration of weight of the product.

Further, incases of food products such as fish, excess water retention leads to unwanted drip loss during thawing of the product. Furthermore, use of chemical agents that are toxic in nature may contaminate the organic products, thereby making them unfit for human consumption.

There is accordingly, a need for an alternate method and device for sterilizing organic products. The alternate method should avoid retention of water in the organic products during sterilization. Further, the alternate method should prevent any deterioration of molecular structure of the organic products during sterilization. Further the alternate method must significantly improve a quality and lifespan of the organic products to minimize economic losses occurring due to spoilages.

SUMMARY OF THE INVENTION

An aspect of the invention provides a method for sterilizing an organic product. The method is performed in a chamber of a sterilization device, having a controlled atmosphere. One or more samples of the organic product is placed inside the chamber for the sterilization. Examples of the organic products include but are not limited to fish, meat, vegetables, fruits, roots, seeds, microbes, fungi, blood plasma and other biodegradable products.

The method includes, introducing a specified quantity of a gaseous composition comprising a predefined proportion of ozone into the chamber. In an embodiment, the ozone is obtained by an ozone generator that is connected to at least one inlet of the chamber via at least one conduit or pipe. The at least one inlet is an airtight opening, that can be opened when the gaseous composition is to be introduced, and can be closed into a sealed position, when no more inflow of the gaseous composition or atmospheric air is required within the chamber. The opening and closing of the at least one inlet is controlled wirelessly by a controller that is communicatively coupled to the at least one inlet.

A flow rate of the ozone through the at least one conduit is controlled via at least one inlet valve provided along the at least one conduit. For example, a controller provides control signals via a wireless communication link, to control an aperture of the at least one inlet valve. Accordingly, an opening or closing of the at least one inlet valve is controlled by the controller. In another embodiment, the at least one inlet valve can be manually operated. Upon introduction of the specified quantity of the gaseous composition, the controller closes the at least one inlet valve, and the at least one inlet of the chamber.

In an embodiment, where the organic product is meat, fish or any product that contains blood, the gaseous composition further comprises a predefined proportion of carbon monoxide (CO) gas. The CO gas is used for carbonizing the organic product to generate carboxymyoglobin. The carboxymyoglobin gives the organic product a bright red color. The red color or hue generated on a surface of the meat gives a visual appeal of freshness.

The method includes, subjecting each sample of the organic product to the gaseous composition present within the chamber and an ultraviolet radiation using at least one ultraviolet tube light provided within the chamber, for a predefined time period to sterilize each sample. In an embodiment, the one or more samples is accommodated on one or more perforated shelves provided inside the chamber. In an embodiment, the at least one ultraviolet tube light is arranged in a manner to radiate an entire surface area of each sample of the organic product accommodated on the each perforated shelf. In an example, an ultraviolet tube light is arranged above each perforated shelf, and a plurality of ultraviolet tube lights are arranged along a top portion of the chamber.

The method further includes maintaining a humidity level of the atmosphere in the chamber in a range of 90 to 100% by using a humidifier unit and the controller. In an embodiment, the humidifier unit measures a current humidity level of the chamber, and provides the humidity level to the controller. The controller compares the current humidity level to a predefined threshold for humidity level, and provides a control signal to the humidifier unit to increase or decrease the humidity level within the chamber incase the current humidity level is lesser or greater than the predefined threshold. Accordingly, the humidifier unit can increase or decrease a rate of passing moisture into the chamber based on the control signal received from the controller.

Further, the method includes maintaining a temperature within the chamber at a desired temperature of −10 to 5 degree Celsius by a plurality of condensers surrounding the chamber. In an embodiment, a temperature sensor provided within the chamber, records the temperature within the chamber and communicates the temperature to the controller. The controller can trigger or switch off cooling of the chamber by the condensers based on the temperature received by the temperature sensor. As a result, the temperature within the chamber is maintained at the desired temperature. For example, the preferred or desired temperature of sterilizing fish fillets of salmon or tuna is −2 degrees Celsius.

In an embodiment, the controller determines operating information of the chamber such as the specified quantity of the gaseous composition, the predefined proportion of ozone, the predefined proportion of carbon monoxide, and the predefined time period for sterilizing the organic product, with a model stored within a memory of the controller. The model comprises operating information for sterilizing a plurality of types and quantities of organic products within the chamber.

In an embodiment, a quantity of samples of the organic product, and a type of organic product is provided as an input to the model, for obtaining the operating information such as the specified quantity and predefined proportions of ozone and CO required for effective sterilization. In an embodiment, the quantity of samples of the organic product and the type of the organic product is provided to the controller via a human machine interface.

The method further includes, releasing the gaseous composition out of the chamber upon completion of the predefined time period, while introducing oxygen and/or atmospheric air into the chamber, until presence of the gaseous composition in the atmosphere of the chamber reaches below a threshold value. The presence of the gaseous composition is detected by one or more sensors provided within the chamber. Level of the gaseous composition is communicated by the one or more sensors to the controller. Based on the level of the gaseous composition, the controller controls the releasing of the gaseous composition and introduction of oxygen into the chamber.

In an embodiment, upon completion of the predefined time period, the controller operates at least one inlet connected to an air purifier unit into an open position so that the oxygen and/or atmospheric air can enter the chamber. The air purifier unit provides the oxygen and/or purified atmospheric air via at least one conduit to the at least one inlet. Further, the controller operates at least one exhaust valve of the chamber, into an open position for venting out the gaseous composition. When the gaseous composition reaches below the threshold value, the at least one inlet and the at least one exhaust valve are closed by the controller. The releasing of the gaseous composition is done, so that procurement of the sterilized one or more samples from the chamber can be done without risk to health of human operators involved in the procurement.

Further, the method includes, opening an exit of the chamber when the gaseous composition is released from the chamber up to the threshold value. The one or more samples are procured through the exit in an insulated arrangement from the chamber. Upon procuring the sterilized samples, each sample is sprayed with a bacteriophages solution, and wrapped in a moisture pad and an antimicrobial paper. The wrapped sample is then vacuum-sealed in a gas permeable bag and then in a high barrier bag (e.g. a nylon bag).

Another aspect of the invention provides a sterilization device for sterilizing an organic product. The sterilization device includes a chamber having a controlled atmosphere, in which one or more samples of the organic product are placed for sterilization. The controlled atmosphere includes a gaseous composition of ozone and/or carbon monoxide in a predefined proportion for sterilization of the organic product. In an embodiment, the chamber is surrounded with a cooling arrangement (e.g. condensers) to maintain a temperature of the chamber in a range of −10 to 5 degree Celsius.

In an embodiment, the chamber comprises an arrangement of shelves to accommodate one or more samples of an organic product. In an embodiment, the arrangement of shelves comprises one or more shelves provided on one or more inner surfaces (e.g. lateral surfaces) of the chamber and/or on either side of at least one metal frame placed in an inner space of the chamber. The one or more shelves are designed to accommodate one or more samples of the organic product. In an embodiment, one or more shelves can be perforated by virtue of having a plurality of holes/perforations. The plurality of holes enables passage of the gaseous composition, for effective interaction of the gaseous composition with the one or more samples accommodated on the shelves. In another embodiment, the arrangement of shelves include a plurality of shelves suspended from a ceiling or top surface of the chamber by metal links, where the plurality of shelves are spaced at a predefined distance from each other to ensure circulation of the gaseous composition around the one or more samples accommodated within the plurality of shelves.

In an embodiment, the one or more shelves are arranged at an inclination to the one or more inner lateral surfaces of the chamber and to the one or more metal frames. Further, an end of each shelf arranged on a lateral surface and the metal frame is connected to a conduit that carries water that condenses on the each shelf into a reservoir. The inclination of the each shelf is adjusted to drain the water that condenses on the each shelf into the conduit. The reservoir is placed on a bottom of the chamber to store the water flowing out of the conduit. In an embodiment, a separate reservoir is provided for each lateral surface and each side of the metal frame to collect water that condenses on shelves provided on the each lateral surface and the metal frame.

The chamber further includes, at least one inlet that permits flow of a specified quantity of the gaseous composition comprising a predefined proportion of ozone gas into the chamber. The ozone gas is used to kill microbes present on the one or more samples. The device includes a controller that determines a specified quantity of the gaseous composition required for sterilizing the one or more samples using a model. The model comprises operating information of the chamber required for sterilization of a plurality types and quantities of organic products. The controller opens the at least one inlet for a first time period to introduce the specified quantity of the gaseous composition into the chamber. In an embodiment, the first time period is determined based on a flow rate of the gaseous composition and the specified quantity of the gaseous composition. The controller closes the at least one inlet, when the specified quantity of the gaseous composition is introduced into the chamber. The controller operates the at least one inlet into a closed position for a predefined time period, so that the specified quantity of the gaseous composition that is introduced into the chamber, interacts and sterilizes the one or more samples during the predefined time period. The predefined time period is determined by the controller using the model, a quantity of the organic product, and a type of the organic product.

In an embodiment, where the organic product includes blood (e.g. meat, fish, poultry) the controller controls introduction of a specified quantity of Carbon Monoxide (CO) gas through the at least one inlet into the chamber for carbonizing the one or more samples of the organic product. Further, the controller determines the specified quantity of the CO gas using the model. In the embodiment, the CO gas is a constituent of the gaseous composition.

In an embodiment, the controller controls the flow rate of the gaseous composition by controlling an aperture of an inlet valve provided within each inlet. In an embodiment, the ozone gas is obtained from an ozone generator that is connected to one or more inlets via one or more first conduits, and the CO gas is obtained from a CO generator, that is connected to one or more inlets via one or more second conduits.

The sterilization device further includes a plurality of ultraviolet tube lights, wherein at least one ultraviolet tube light is arranged above each shelf and along a top portion of the chamber. The ultraviolet tube light emits ultraviolet radiation to sterilize the one or more samples of the organic product. In an embodiment, the controller switches on one or more of the plurality of ultraviolet tube lights based on a placing of the one or more samples in the chamber for the predefined time period.

Further, the chamber includes least one outlet through which the gaseous composition is vented out of the chamber upon sterilization of each sample, wherein the outlet is opened after a time period required for the sterilization is complete. In an embodiment, the at least one outlet is an exhaust valve, having an exhaust fan that pulls out the gaseous composition or any air present within the chamber. The controller opens the at least one outlet and the at least one inlet, upon completion of the predefined time period, to release the gaseous composition out of the chamber through the at least one outlet, and introduce atmospheric air into the chamber through the at least one inlet simultaneously, until a presence of the gaseous composition in the chamber reaches below a threshold value. The at least one inlet and the outlet are kept open until a presence of the gaseous composition in the chamber reaches below a threshold value.

In an embodiment, the atmospheric air is obtained from an air purifier unit coupled to the at least one inlet via at least one third conduit. The controller controls a flow rate of the atmospheric air by controlling an aperture of an inlet valve, provided within each inlet. For example, the controller controls a flow rate of the atmospheric air from the air purifier unit into the chamber, by controlling an aperture of an inlet valve provided within an inlet, where the air purifier unit is connected to one or more inlets via one or more third conduits.

The controller further maintains a humidity level of the atmosphere in a range of 90-100% using a humidifier unit, where the humidifier unit provides humidity into the atmosphere based control signals received from the controller.

The chamber also includes an exit that opens upon releasing the gaseous composition up to the threshold value from the chamber. The one or more samples is removed from the chamber upon completion of the sterilization, through the exit in an insulated arrangement. In an embodiment the exit is an air tight sealed door, operable by the controller.

DETAILED DESCRIPTION

The present invention is related to methods of sterilizing organic products, by a sterilization device, wherein the organic products include at least one of fish, meat, vegetables, fruits, roots, seeds, microbes, fungi and blood plasma. Disclosed methods of sterilization result in minimal microbes in the tank, For example, the sterilization device is used for sterilizing fish fillets, prior to freezing of the fish fillets, in a fish process plant. In an embodiment, the organic products can include blood plasma. Various embodiments of the present invention can be practiced using the sterilization device as shown in FIG. 1.

Figure 1:
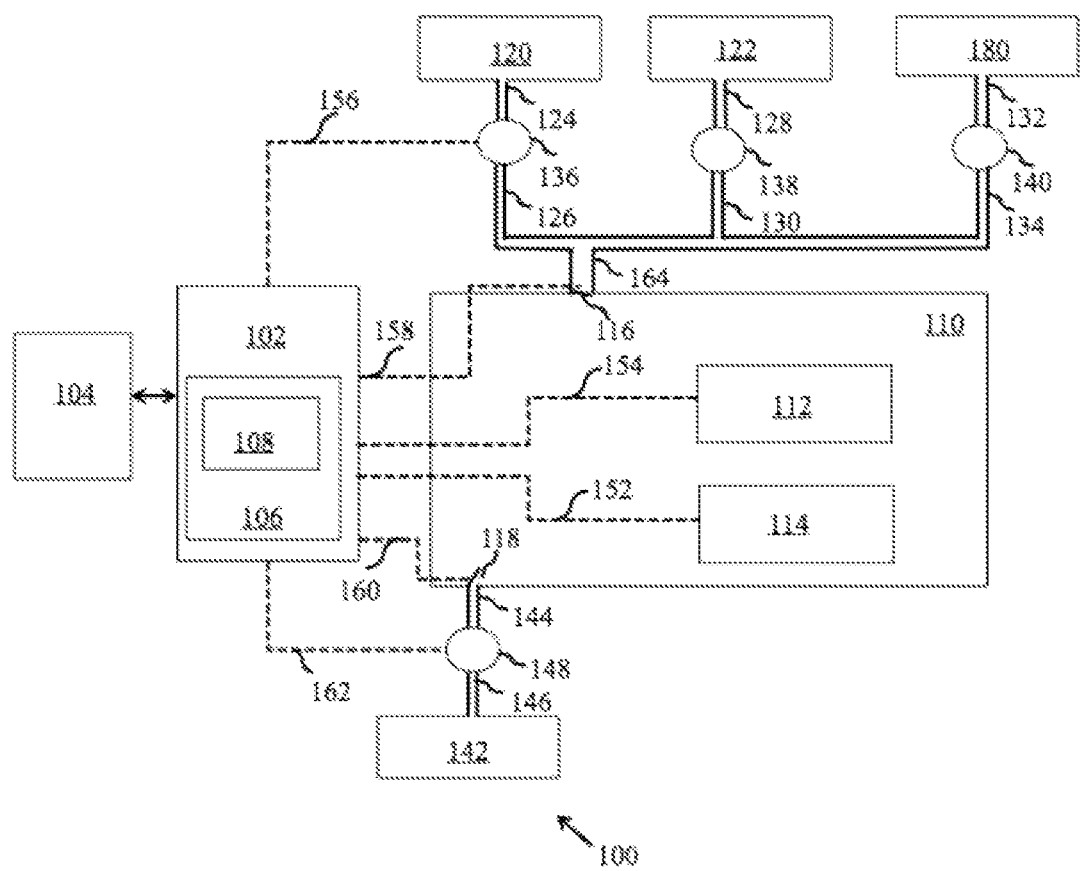
FIG. 1 is a schematic diagram illustrating components of a sterilization device arranged, in accordance with an embodiment of the present invention.

FIG. 1 is a schematic diagram illustrating various components of a sterilization device 100, in accordance with an embodiment of the present invention. As shown in FIG. 1, the sterilization device 100 includes a chamber 110, a controller 102, a human machine interface (HMI) 104, a humidifier unit 112, a plurality of sensors 114, an ozone generator 120, a carbon monoxide (CO) generator 122, an air purifier unit 180, and an exhaust unit 142.

The chamber 110 is an enclosed structure inside which one or more samples of an organic product are introduced for undergoing sterilization. The chamber includes a controlled atmosphere required for the sterilization. In an embodiment, the chamber is surrounded with a cooling arrangement (e.g. condensers or cooling coils that circulate a refrigerant) to maintain a temperature of the chamber in a range of −10 to 5 degree Celsius. The low temperature of the chamber helps in retarding microbial growth in the samples of the organic product during the sterilization process.

Figure 2A:
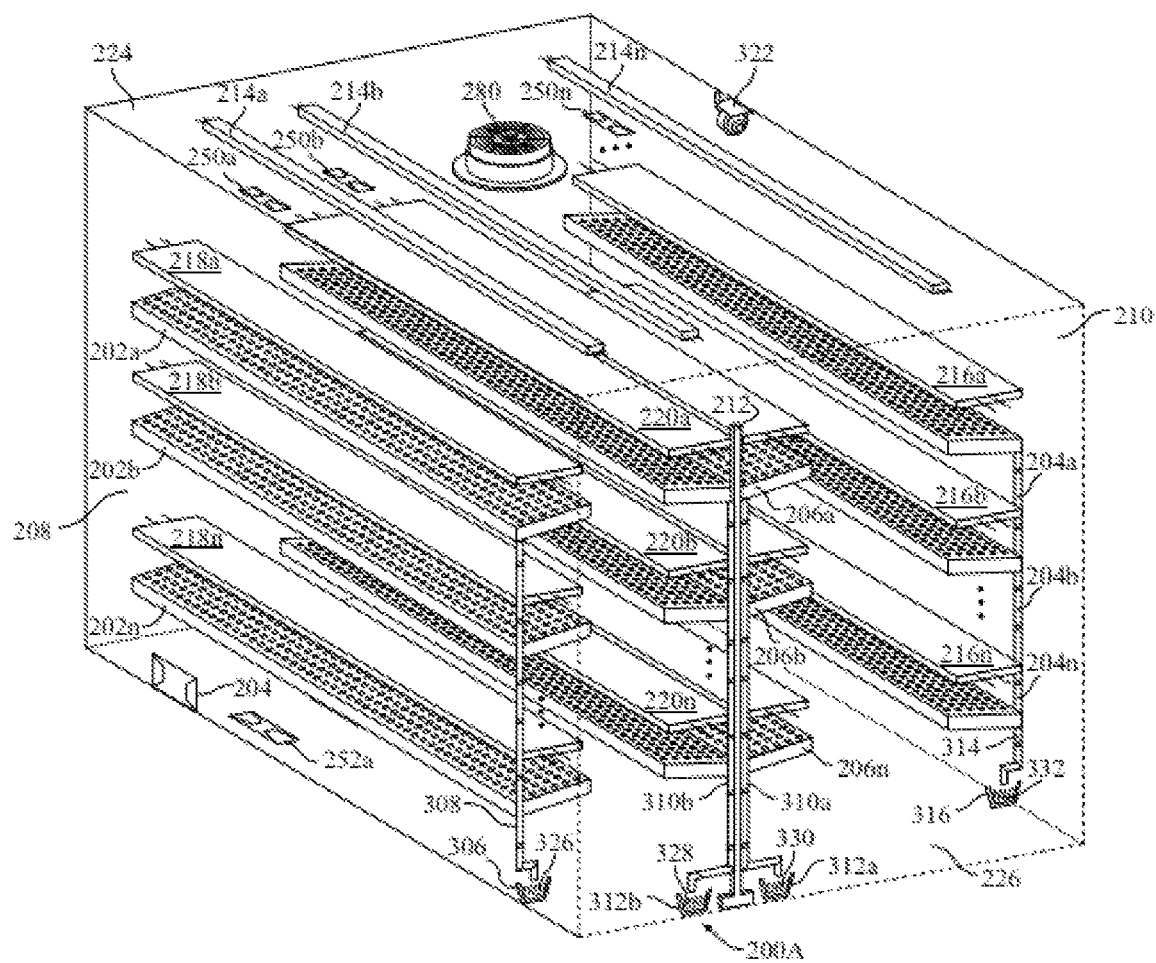
FIG. 2A is a perspective view of a chamber of the sterilization device of FIG. 1, in accordance with an embodiment of the present invention.
Figure 2B:
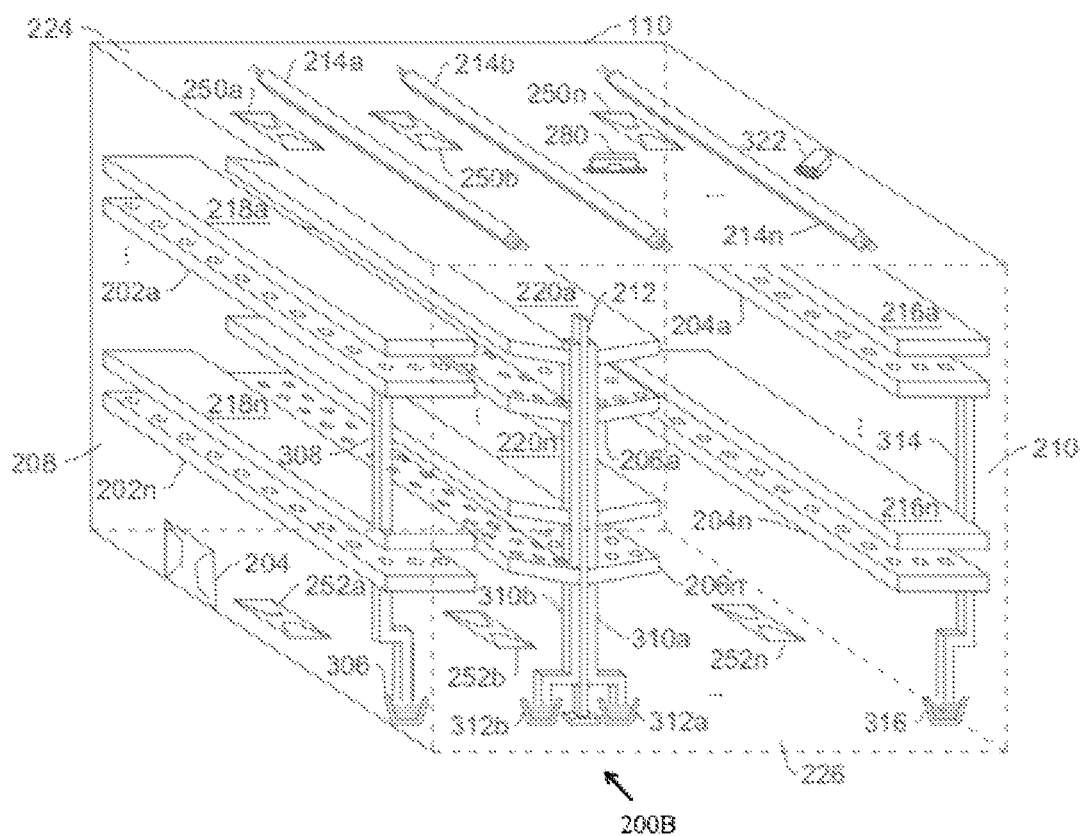
FIG. 2B is a perspective view of a chamber of the sterilization device of FIG. 1, in accordance with another embodiment of the present invention.

The chamber includes an arrangement of shelves to accommodate the one or more samples of the organic product. In an embodiment, the arrangement of shelves includes one or more shelves provided on one or more inner lateral surfaces of the chamber (for example, shelves 202a-n and 204a-n, as shown in FIGS. 2A-2B). Additionally, one or more shelves (for example, shelves 206a-n as shown in FIG. 2A-2B) may be provided on either side of at least one metal frame (for example, metal frame 212, as shown in FIGS. 2A-2B), where a metal frame is placed in an inner space of the chamber. Further, each shelf (e.g. 202a, 202b up to 202n as shown in FIG. 2) is arranged at an inclination to facilitate collection of water that condenses on the each shelf into a reservoir (e.g. reservoir 306 as shown in FIGS. 2A-2B) placed below the each shelf (e.g. reservoir 306 is placed below 202a, 202b up to 202n, as shown in FIGS. 2A and 2B). The reservoir (e.g. 306) receives the water (e.g. 326) via a conduit (e.g. 308) that is connected to one end of the each shelf.

The chamber includes at least one inlet to permit flow of a gaseous composition comprising a predefined proportion of ozone into the chamber. In an embodiment, where the organic product includes blood (e.g. meat, fish, and poultry products), the gaseous composition also includes CO gas. An opening or closing of the at least one inlet can be controlled by signals provided by the controller through a communication link (for example, as shown in FIG. 1, inlet 116 is controlled by the controller via communication link 158). In an embodiment, the controller opens the at least one inlet for a first time period to introduce the specified quantity of the gaseous composition into the chamber. The first time period is determined based on a flow rate of the ozone gas, a flow rate of the CO gas and the specified quantity of the gaseous composition. Upon introduction of the specified quantity of the gaseous composition into the chamber, the controller closes the at least one inlet for a predefined time period during which the one or more samples are exposed to the ozone and CO gas.

The predefined proportion of the ozone gas is obtained from the ozone generator that is connected to one or more inlets via one or more first conduits. In an embodiment, the flow rate of the ozone gas can be controlled by controlling an aperture of one or more inlet valves coupled to the one or more first conduits. Similarly, the predefined proportion of CO gas is obtained from the CO generator via one or more second conduits that connect the CO generator to one or more inlets of the chamber. In an embodiment, the flow rate of the CO gas can be controlled by controlling an aperture of one or more inlet valves coupled to the one or more second conduits. In an embodiment, the one or more inlets through which the ozone gas is introduced is separate and distinct from the one or more inlets through which the CO gas is introduced. In such embodiment, an inlet valve may be provided within each inlet to control the flow rate of ozone and CO gas as applicable. In another embodiment, the one or more inlets through which the ozone gas is introduced is same as the one or more inlets through which the CO gas is introduced. In such embodiment, the inlet valve is provided within each conduit that carries the ozone gas or CO gas.

For example, as shown in FIG. 1, the chamber includes an inlet 116 through which a specified quantity of gaseous composition comprising the predefined proportion of ozone gas and the predefined proportion of CO gas is introducing into the chamber for sterilization.

The ozone gas is obtained from the ozone generator 120 via a first conduit 124, 126. A flow rate of the ozone gas through the first conduit 124, 126 depends on a degree of opening of an aperture of the inlet valve 136 provided within the first conduit 124,126. In an embodiment, the inlet valve is an electromechanical valve that can be operated by the controller. As shown, the controller may provide control signals via a communication link (CL) 156 (e.g. Bluetooth™ or any wireless communication link) to control the opening of the inlet valve. Similarly, the CO gas is obtained from the CO generator 120 via a second conduit 128, 130. A flow rate of the CO gas through the second conduit 128, 130 depends on a degree of opening of an aperture of the inlet valve 138 provided within the second conduit 128,130. In an embodiment, the inlet valve 138 is an electromechanical valve that can be operated by the controller. The controller may provide control signals via wireless communication links (not shown in FIG. 1) to control the opening of the inlet valve 138. The first conduit 126 and the second conduit 130 join both join a conduit 164 that is connected to the inlet 116. Thus the ozone gas and the CO gas flow together through the conduit 164 to the inlet 116, and into the chamber.

In an embodiment, the air purifier unit 180 is connected to one or more inlets of the chamber via one or more third conduits. The air purifier unit supplies atmospheric air (purified) or oxygen into the chamber via the one or more inlets, when the sterilization is complete, and the chamber needs to be refilled with atmospheric air. In an embodiment (as shown in FIG. 1) the air purifier unit is connected to the inlet 116 via a third conduit 132, 140. A flow rate of the atmospheric air through the third conduit 132, 134 depends on a degree of opening of an aperture of the inlet valve 140 provided within the third conduit 132, 134. In an embodiment, the inlet valve 140 is an electromechanical valve that can be operated by the controller. The controller may provide control signals via wireless communication links (not shown in FIG. 1) to control the opening of the inlet valve 140.

The chamber further includes at least one outlet through which the gaseous composition is vented out of the chamber upon sterilization of each sample. In an embodiment, the controller controls an opening and closing of the at least one outlet. In an example, as shown in FIG. 1, the chamber includes one outlet 118, through which the gaseous composition is vented out through a conduit 144, 146 into the exhaust unit 142. The exhaust unit can be a reservoir that stores the gaseous composition that is vented out of the chamber. In an embodiment, the outlet 118 can open to an external environment.

In an embodiment, the controller can open the at least one outlet and the at least one inlet upon completion of the predefined time period to release the gaseous composition from the chamber through the at least one outlet, and introduce the atmospheric air obtained from the air purifier unit into the chamber through the at least one inlet simultaneously, until a presence of the gaseous composition in the chamber reaches below a threshold value. In the example, shown in FIG. 1, the controller can operate the inlet valve 140, and the inlet 116 into an open position, for introducing the atmospheric air into the chamber, and at the same time, operate the outlet 118 and the exhaust valve 148 into an open position for venting out the gaseous composition from the chamber. It is understood, that during the venting out process, the inlet valve 136 and the inlet valve 138 are kept in a closed position to prevent additional ozone gas and CO gas from entering the chamber.

The chamber can further include, a plurality of ultraviolet (UV) tube lights for exposing the one or more samples to UV radiation for sterilization purpose. It is known that an UV tube light emits UV radiation to sterilize at least the one of the one or more samples of the organic product by killing/destroying multiple pathogens and microbes thriving in the organic product. In an embodiment, at least one UV tube light is arranged above each shelf of the arrangement of shelves within the chamber. For example, as shown in FIGS. 2A and 2B, UV tube light 218a is arranged above the shelf 202a. Similarly, UV tube lights 212b-n is arranged above shelves 202b-n. Similarly, UV tube lights 220a-n are arranged on either side of the metal frame and over the plurality of shelves 206a-n. Further, at least one UV tubelight is arranged along a top portion of the chamber. For example, as shown in FIG. 2A UV tube lights 214a-n are arranged along a top portion (224) of the chamber (110).

The controller switches on one or more of the plurality of ultraviolet tube lights for the predefined time period for sterilizing the one or more samples of the organic product with the UV tube light. It is understood, that the one or more samples are also exposed to the gaseous composition during the predefined time period. The one or more UV tube lights to be switched on is selected based on a placing of the one or more samples in the chamber. For example, is the one or more samples of the organic product are accommodated on shelves 202a-b, 206a-b and 204a-b, then only the UV tube lights 218a-b, 220a-b, 216a-b and additionally 214a-n may be switched on for sterilizing the samples with the UV radiation, as the UV radiation from remaining UV tubelight present in the chamber may not reach the samples.

The controller 102 is programmable logic controller (PLC) that is programmed using a model 108 stored within a memory 106 of the controller. The model comprises a plurality of operating information required for operating the sterilization device for sterilizing a plurality of types of organic products. In an embodiment, the model includes a temperature of the chamber, a pressure, a humidity range, a specified quantity of a gaseous composition comprising a predefined proportion of ozone gas and a predefined proportion of CO gas required for sterilization of the plurality of types and quantities of organic products. For example, an entry within the model can include operating information for sterilizing 50 kgs of tuna fillets in a chamber of size 4 meters*4 meters*2.5 meters, where the operating information includes a predefined proportion of 15 ppm of ozone, 10 ppm of CO, a humidity of 99%, a temperature of –2 degree Celsius, and a predefined time period of 30 minutes for sterilizing the tuna fillets.

The controller builds the model using history data of operating information associated with sterilizing the plurality types and quantities of the organic products within the chamber. The history data is procured over a period of time during which the plurality types of organic products is sterilized within the chamber. In an embodiment, the operating information associated with a first quantity of a particular type of organic product, is extrapolated by way of direct proportion to determine the operating information for a plurality of quantities of the particular type of organic product. Accordingly, the operating information for the plurality of types of organic products is derived and stored in the model. In cases where real time operating information of an example organic product is unavailable, the operating information is derived from operating information available for similar types of organic products. Organic products are classified as similar organic products based on predefined physiological and chemical properties (e.g. a fat content, water content, a toughness of constituent fibers, and a chemical composition).

For example, one or more organic products are grouped into a category based on similar physiological and chemical properties. Operating information of organic products belonging to a particular category usually does not deviate by more than a threshold level. Hence, when the real-time operating information of an example organic product is unavailable, a category of the organic product is determined from the model. Further, a standard deviation is applied to operating information applicable to the category to obtain the operating information for sterilizing the example organic product. Aforesaid grouping of organic products into categories is known to derive accurate operating information required for sterilizing the organic products. Use of the model, reduces human dependence during the sterilization process, thereby avoiding errors (e.g. human error) that can deteriorate an overall quality of the organic product undergoing sterilization.

Accordingly, the controller determines operating information required for sterilizing the one or more samples of the organic product introduced into the chamber using the model when a quantity of samples of the organic product and a type of the organic product is provided as an input to the model. In an embodiment, the quantity of samples of the organic product and the type of the organic product is received via an input interface 104 coupled to the controller. For example, the input interface is a human machine interface (HMI) via which an operator can provide the input to the controller regarding a type of the organic product to sterilize, and a quantity of samples of the organic product to be fed into the chamber for sterilization. The controller can determine the operating information required for the organic product using the model stored within the memory of the controller. Typically, the input is provided to the model when the one or more samples is introduced into the chamber.

The controller controls opening/closing of the inlet valves 136-140, the inlet 116, the outlet 118 and the exhaust valve 148 via communication links based on the operating information received by the model. For example, upon receiving the operating information such as the predefined time period, the specified quantity of the gaseous composition, the predefined proportion of the ozone gas and the predefined proportion of the CO gas, from the model, the controller can operate the opening of the inlet 116, and the inlet valves 136 and 138 into an open position and close position depending on the operating information. For example, the inlet 116 is kept open for a first time period to introduce the specified quantity of the gaseous composition into the chamber, wherein the first time period is determine by the controller based on a flow rate of the ozone gas, a flow rate of the CO gas and the specified quantity of the gaseous composition. Similarly, upon introduction of the gaseous composition, the controller, keeps the inlet 116 and the inlet valves 136 and 138 into a closed position until lapse of the predefined time period. Further, the controller moves the outlet into an open position to vent out the gaseous composition, until a level of the gaseous composition falls below the threshold value. In an embodiment, sensors placed within the chamber determine the level of the gaseous composition in the chamber, and communicate the same to the controller. In an embodiment, the communication links are wireless communication links, through which controller communicates/sends wireless control signals for the opening or closing the inlet 116, the outlet 118 and the inlet valves 136-140 and the exhaust valve 148.

The controller controls the humidity level within the chamber based on the operating information received form the model. In an embodiment, a humidity sensor of the plurality of sensors installed within the chamber measures the humidity level in the chamber and communicates the measured humidity level via communication link 152 to the controller. In case the humidity level is lower than the humidity range provided within the operating information, the controller can send control signal to the humidifier unit via communication link 154, to increase the moisture level. The humidifier unit can provide moisture into the chamber by a fogger, to increase the humidity level up to the humidity range provided within the operating information.

Similarly, the controller can monitor a temperature of the chamber using the plurality of sensors. The controller compares a temperature measured by a temperature sensor with the temperature provided in the operating information. Incase the temperature is higher or lower than the operating temperature required, the controller can communicating control signals to the condensers coupled to the chamber to decrease or increase the temperature respectively.

Though the chamber 110 is shown to include one inlet 116, and one outlet 118, it is understood that the chamber 110 may include multiple inlets and multiple outlets. In an embodiment, the chamber is an airtight sealed room, and the inlets and the outlets are openings provided along walls of the room. In an embodiment, the chamber is made of stainless steel. In an embodiment, dimensions of the chamber include 4 meters of length, 4 meters of width and 2.5 meter of height. Perspective views of the chamber is provided in FIG. 2A-2B.

FIG. 2A shows a perspective view 200A of the chamber 110 of FIG. 1, according to an embodiment of the present invention. FIG. 2B shows another perspective view 200B of the chamber 110, according to an embodiment. As shown, in FIGS. 2A and 2B, the chamber is a rectangular structure having the plurality of shelves 202a-n, and 204a-n, provided on a lateral surface 208, and 210 respectively of the chamber. While the plurality of shelves are shown only on two lateral surfaces, it is understood that, a plurality of shelves can be provided on a front surface and rear surface of the chamber. The chamber also includes the plurality of shelves 206a-n provided on either side of the metal frame 212 placed within an inner space of the chamber. In an example, the metal frame is a steel frame that can host a plurality of shelves. It is understood, that multiple such metal frames may be placed within the inner space of the chamber. Further, each shelf is designed to accommodate one or more samples of the organic product as shown in a cross-sectional front view of the chamber in FIG. 3.

Figure 3:
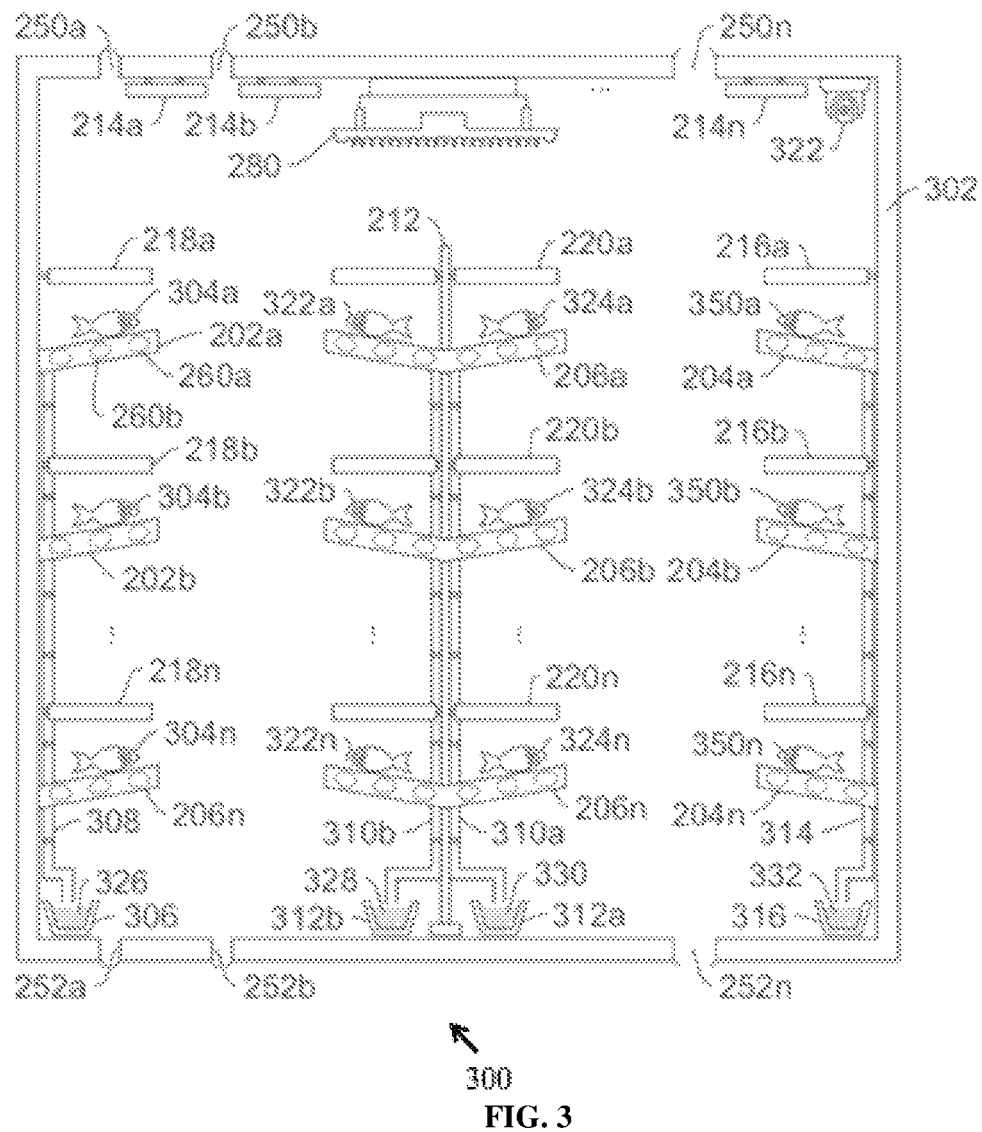
FIG. 3 is a cross-sectional front view of the chamber of FIG. 1, in accordance with an embodiment of the present invention.

FIG. 3 illustrates a cross sectional front view 300 of the chamber 110, according to an embodiment of the present invention. As shown, the shelves 202a-n accommodates samples 304a-n, shelves 206a-n accommodate samples 322a-n, and 324a-n, and shelves 204a-n accommodate samples 350a-n. Though each shelf is shown to accommodate only one sample of the organic product, it is understood that the each shelf can accommodate multiple samples depending on a size of the sample and dimension of the each shelf.

In an embodiment, each shelf is a 6 millimeter toughened glass fitted into the steel frame. The plurality of shelves 206a-n are arranged such that a distance between two consecutive shelves is adjustable depending on a size of a sample accommodated on the shelves. For example, a distance of 8 inches can be maintained between the plurality of shelves. In an embodiment, adjustable supports (not shown) are provided every 36 inches along a length of each shelf.

The plurality of shelves is arranged at an inclination (e.g. a slight angle) to the one or more inner surfaces of the chamber and to the one or more metal frames placed in the inner space of the chamber. The inclination of each shelf is adjusted so that water that condenses on the shelf can be accumulated on one side of the shelf, before being drained off through a plurality of conduits into a reservoir/a removable container (e.g. 312a-b, 306, and 316). For example, the shelves 202a-n are connected to a conduit 308, to drain water into the reservoir 306. As shown the reservoir 306 stores water 326. Similarly, 310a-b collects water drained off shelves 206a-n into reservoir 312a and 312b respectively. As shown, reservoir 312a stores water 328 and reservoir 312b stores water 330. Similarly, conduit 314 drains water collected from shelves 204a-n into the reservoir 316. As shown, reservoir 316 stores water 332. In an embodiment, the plurality of conduits is made of steel.

The plurality of shelves is used to accommodate one or more samples of the organic product to sterilize. The one or more samples, a placed spaced out on a shelf. For example, fish fillets may be placed spaced out on a shelf. In an embodiment, each shelf is perforated or is provided with multiple holes. As shown, shelf 202a has a plurality of holes 260a-n. A top view of shelf 202a is shown in FIG. 4.

Figure 4:
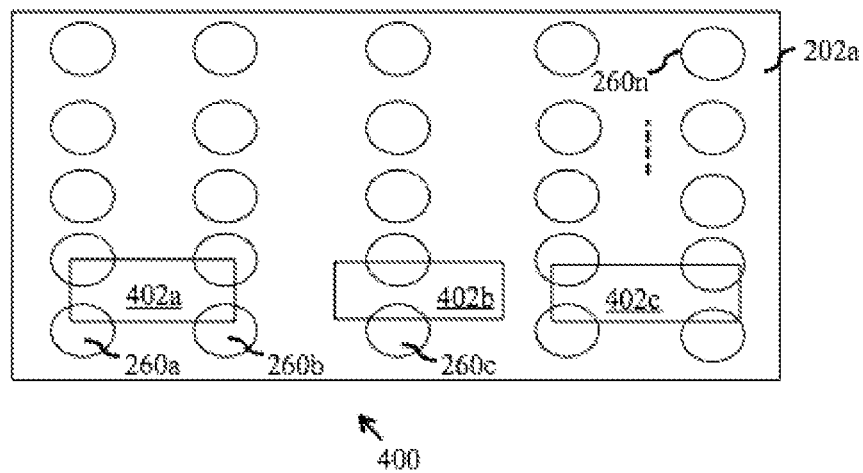
FIG. 4 is a top view of a perforated shelf used for accommodating one or more samples of the organic products, in accordance with an embodiment of the present invention.

FIG. 4 illustrates a top view 400 of the shelf 202a. As shown, the perforated shelf 202a includes a plurality of holes 260a-n. A set of samples 402a-c of an organic product (e.g. fish) is placed spaced out on the perforated shelf. The plurality of holes, facilitate exposure of a bottom portion of each sample to the gaseous composition, thereby enabling effective sterilization.

Referring to FIG. 3, in an embodiment, the chamber is surrounded by an insulation material (e.g. polyurethane foam) 302. The insulation prevents external heat from entering the chamber, and thereby facilitates maintaining the chamber at a desired temperature. The chamber is surrounded with a cooling arrangement (not shown) to maintain a temperature of the chamber in a range of −10 to 5 degree Celsius. For example, for a chamber of size 4 m*4 m*2.5 m, condensers of size 30 inches*30 inches*24 inches and 100 kilograms (kgs) weight are used to maintain a temperature of −2 degree Celsius within the chamber.

Further, referring to FIGS. 2A and 2B, the plurality of ultraviolet (UV) tube lights 214a-n is arranged along the top surface 224 of the chamber. Further, the plurality of UV lights 218a-n are arranged along the lateral surface 208, such that at least one UV light is placed above a shelf (e.g. 218a is arranged above shelf 202a). Similarly the plurality of UV lights 216a-n is arranged on another lateral surface 210. As shown, 216a-n are arranged above the shelves 204a-n. Further, the plurality of UV tube lights 220a-n are arranged above shelves 206a-n on the metal frame 212. In another embodiment, (not shown in FIGS. 2A and 2B) the UV tube lights can be above and below each shelf in a dispersed manner, to ensure the each portion of each sample receives the UV radiation.

The chamber includes one or more light sources (e.g. LED tube lights) (not shown in the FIGS. 2A and 2B) to radiate visible light for illuminating the chamber. Illumination is required, within the chamber during introducing the organic product into the chamber, and during removal of the organic product upon completing sterilization of the organic product. In an embodiment, the chamber includes light sources on the top portion of the chamber. In another embodiment, a plurality of light sources may be provided on a lateral surface of the chamber. Any suitable arrangement of the one or more light sources that illuminate the chamber from within can be envisaged.

Further, as shown, a plurality of inlets 250*a-n* is provided on the top surface 224 of the chamber. The inlets are connected to an ozone generator (e.g. 120) and/or a carbon monoxide (CO) generator (e.g. 122) via conduits for receiving the gaseous composition. Further, as shown the chamber includes a plurality of outlets 252*a-n*, on a bottom surface 226 of the chamber. In an embodiment, the plurality of outlets 252*a-n* can be provided on a front surface of the chamber, and the plurality of inlets 250*a-n* can be provided on a rear surface of the chamber.

Further, the chamber also includes a partition (not shown) herein. The partition divides the chamber into two parts. In an embodiment, the partition is an air tight door, that isolates one part of the chamber from another part. The partition is used when only a part of the chamber is to be used for sterilization. For example, if a load of the organic product is less, and a part of the chamber is sufficient to accommodate the load, then the partition may be used to close off the other part of the chamber. As a result, the process of sterilization is made efficient and faster.

Further, the chamber includes a camera 322 or any such image-capturing device installed on the top surface of the chamber. The camera 322 is provided, to capture images of the one or more samples of the organic product during the sterilization process. Though FIGS. 2A and 2B include a single camera, multiple cameras at various locations of the chamber can be used. In an embodiment, the camera can be a rotating camera that rotates to capture images in a plurality of directions around it. The camera 322 is wirelessly coupled to the controller, and the HMI, thereby an operator may view a condition of the chamber and the samples during the sterilization process. Such view enables the operator to prevent an error condition from propagating. For example, incase due to an error, the samples, turn red prior to the predefined time period, the operator may choose to discontinue the sterilization process by opening the at least one outlet for venting out the gaseous composition from the chamber, and provisioning atmospheric air into the chamber via the at least one inlet.

The chamber may also include a circulating device 280 (e.g. a fan) to circulate the gaseous composition and air present within the chamber. Such circulation facilitates movement of the ozone and CO gas throughout the chamber, thereby effecting uniform sterilization of the organic product across the chamber. In an embodiment the circulating device is positioned on the top portion 224 (e.g. ceiling of a room in case the chamber is a room) of the chamber. In another embodiment, the circulating device can be positioned on the lateral surface 208 or 210 of the chamber. Alternatively, the circulating device can be position on the front or rear surface of the chamber. In another embodiment, a plurality of circulating devices, located at multiple locations within the chamber can be used.

In an embodiment, a speed of operation of the circulating device is based on a control signal provided by the controller. In another embodiment, the speed of operation of the circulating device is manually controlled. In an embodiment, a single fan (as shown in FIGS. 2A and 2B) is used for circulating the gaseous composition. A perspective view of the circulating device is shown in FIG. 5A.

Figure 5A:
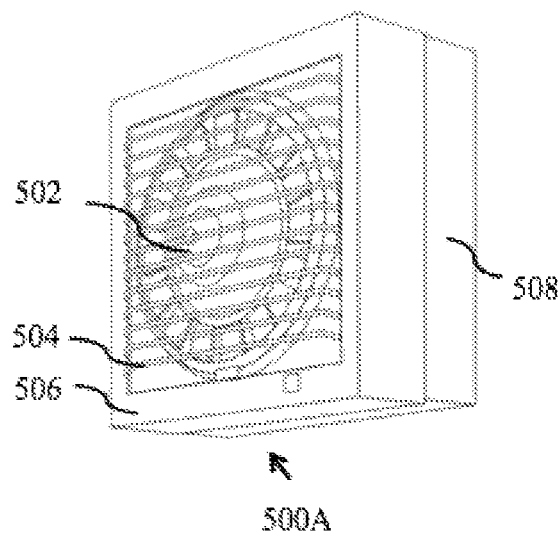
FIG. 5A is a bottom view of a circulating fan used within the chamber of FIG. 2A-2B, in accordance with an embodiment of the present invention.

FIG. 5A is a perspective view 500A of the circulating device 280, according to an embodiment of the present invention. As shown the circulating device includes a fan 502 that rotates within a metal cage 504. The fan is supported within a base 506, which includes the circuitry involved in rotating the fan. The base 506 is made of a solid metallic material, and is supported over a metallic frame 508. The metallic frame and can be affixed to a ceiling or a wall, for installing the circulating device. For example, as shown in FIGS. 2A-2B, the circulating device 280 is installed on the top portion of the chamber. In FIGS. 2A and 2B, the base 508 is shown affixed to the top portion of the chamber, where the fan 502 faces towards the bottom surface 226 of the chamber. A bottom view of the circulating device 280 is shown in FIG. 5B.

Figure 5B:
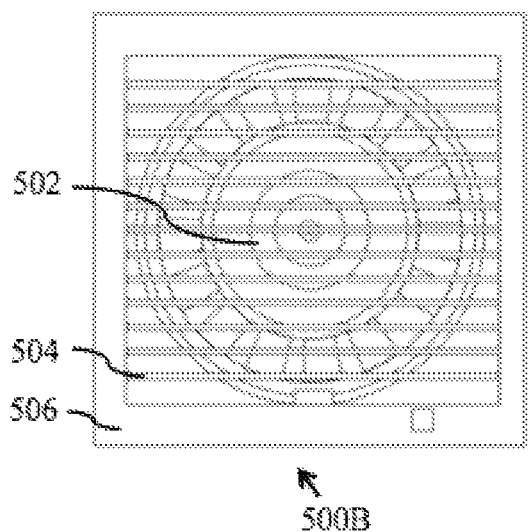
FIG. 5B is a front view of a circulating fan used within the chamber of FIG. 2A-2B, in accordance with an embodiment of the present invention.

FIG. 5B illustrates a bottom view 500B of the circulating device 280. As shown, the fan 502 is enclosed within the cage 504. To illustrate the fan clearly, a front view is shown in FIG. 5C.

Figure 5C:
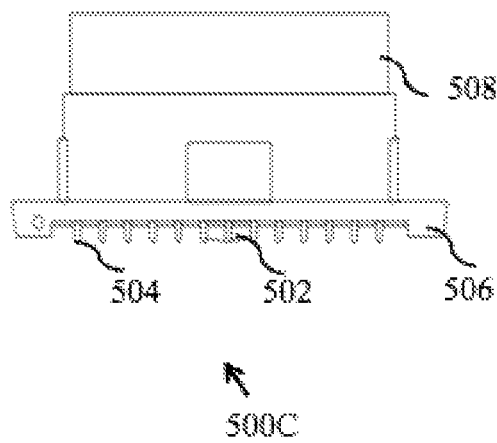
FIG. 5C is a perspective view of a circulating fan used within the chamber of FIG. 2A-2B, in accordance with an embodiment of the present invention.

FIG. 5C is a front view 500C of the circulating device 280 used within the chamber of FIG. 2A-2B, in accordance with an embodiment of the present invention. The front view of the circulating device is depicted in FIG. 3.

Referring to FIGS. 2A and 2B, the chamber also includes an exit 204, from where the one or more samples of the organic product are introduced and taken out of the chamber. In an embodiment, light emitting diode (LED) tube lights (not shown) may be provided on a top portion of the chamber to ensure illumination inside the chamber. The LED may be operated via an ON/OFF switch provided on the HMI coupled to the controller.

Figure 6:
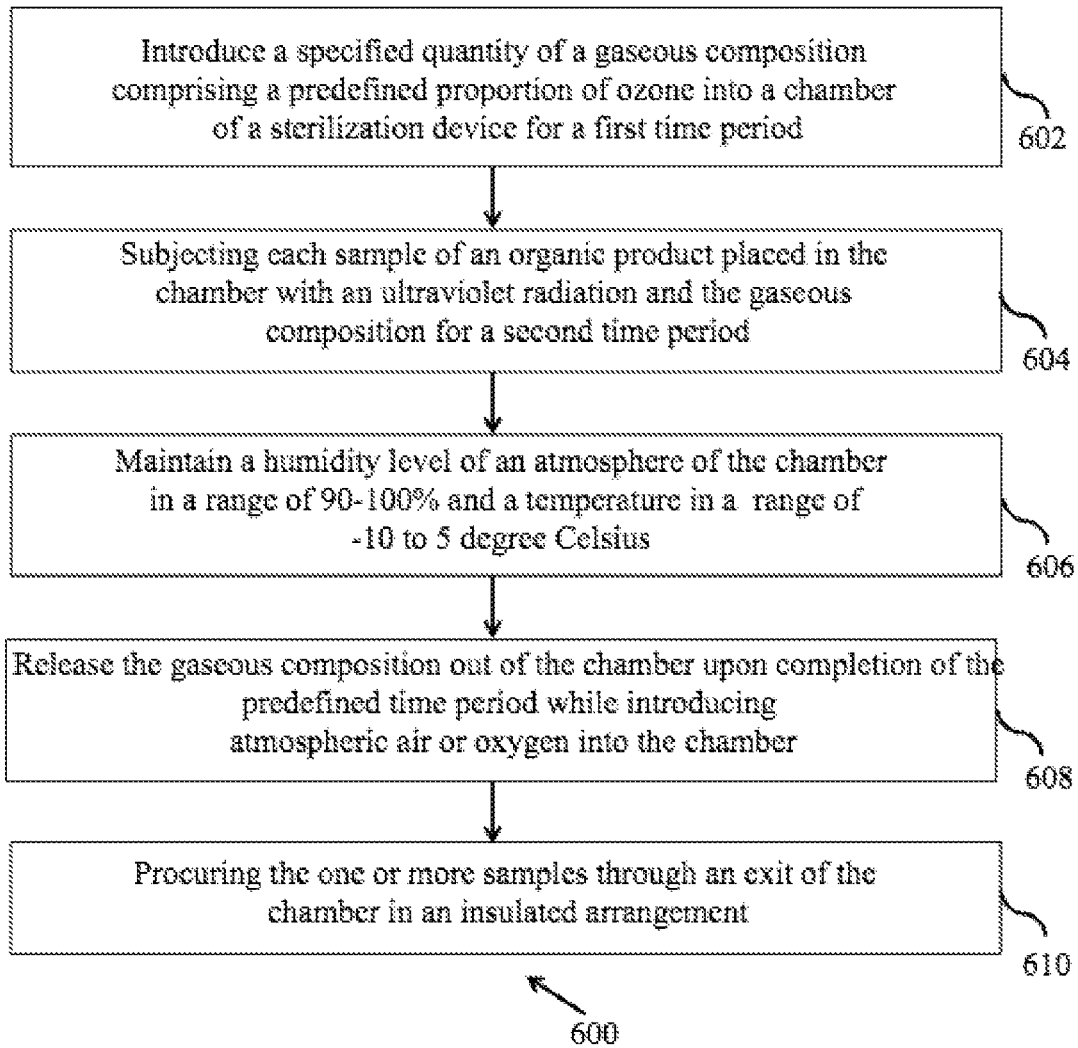
FIG. 6 is a flowchart of a method for sterilizing one or more samples of an organic product in a chamber of a sterilization device, in accordance with an embodiment of the present invention.

Each of the components of the sterilization device performs one or more steps of a method for sterilizing organic product(s), as disclosed in FIG. 6.

FIG. 6 is a flowchart 600 of the method for sterilizing one or more samples of an organic product in a process plant (e.g. sterilizing fish in a fish processing plant). The method may be performed with a sterilization device (e.g. 100). Sterilizing includes killing microbial growth present in one or more samples of the organic products placed within a chamber (e.g. 110) of the sterilization device. The chamber is arranged to have a controlled atmosphere, for said sterilization.

At step 602, a specified quantity of a gaseous composition comprising a predefined proportion of ozone and/or a predefined proportion of carbon monoxide (CO) gas is introduced via at least one inlet (e.g. 116) into the chamber for a first time period. Ozone gas is introduced to sterilize the one or more samples. For example, in case of fish fillets, ozone gas is effective in killing bacteria such as salmonella, listeria and the like. A concentration of 2 parts per million (ppm) of ozone is sufficient to kill pathogens existing in the organic products. Further, CO gas is used to generate a red hue on a surface of an organic product that contains blood. For example, CO gas interacts with blood present in a fish sample to generate a red color on a surface of the fish sample. The red color gives visual effect of freshness of the fish sample.

In an embodiment, a flow of the ozone is controlled via at least one inlet valve (e.g. 136). In an embodiment, the ozone and CO is obtained from an ozone generator (e.g. 120) and a CO generator (e.g. 122) respectively, via at least one conduit (e.g. 124). A controller (e.g. 102) controls a flow rate of the ozone and CO gas by controlling an aperture of the at least one inlet valve. The controller also controls a first time period for which the at least one inlet is kept open. The controller, based on a flow rate of the gaseous composition, determines the first time period. Upon completion of the first time period, the controller, sends control signals to the at least one inlet to close into an airtight position, so that no more ozone gas and/or CO gas enters the chamber.

The controller determines, the specified quantity of the gaseous composition, the predefined proportion of ozone, and the predefined proportion of carbon monoxide, and a predefined time period for which the ozone and CO gas need to interact with the organic product, by using a model (e.g. 108), that is stored within a memory (e.g. 106) of the controller, a quantity of samples of the organic product, and a type of organic product. The quantity of samples of the organic product and the type of the organic product is provided to the controller via a human machine interface (HMI) (e.g. 104). In an embodiment, the model comprises operating information of the chamber required for sterilization of a plurality of types of organic products of various quantities. The operating information includes a quantity of Ozone and Carbon Monoxide, required for sterilizing and carbonizing a particular quantity of an organic product and a predefined time period for which the Ozone and the Carbon Monoxide need to interact independently with the quantity of the organic product in a controlled temperature and humidity to achieve effective sterilization and carbonizing. For example, the model may include operating information of 15 ppm of ozone, 10 ppm of CO, and a first time period of 30 minutes for sterilizing and carbonizing 50 kgs of tuna fillets in the chamber.

At 604, one or more samples of the organic product is subjected to an ultraviolet radiation using a plurality of ultraviolet tube lights, and the gaseous composition for the predefined time period to sterilize the each sample. The controller switches on one or more of the plurality of ultraviolet tube lights based on a placing of the one or more samples in the chamber. The one or more UV lights are kept on for the predefined time period. Further, the at least one inlet is kept closed during the predefined time period.

In an embodiment, the one or more samples is accommodated on one or more shelves (e.g. perforated shelves) provided inside the chamber, wherein one or more ultraviolet tube lights are arranged above each shelf to radiate an entire surface area of a set of samples of the organic product accommodated on the each shelf. In an embodiment, the shelves are perforated or have a plurality of holes, so that the gaseous composition can come in contact with a surface of a sample that faces the shelf. The shelves are made of toughened glass or any other transparent material that can pass the UV radiation.

At 606, the controller maintains a humidity level of the atmosphere in the chamber is maintained in a range of 90 to 100% by using a humidifier unit (e.g. 112). Further, the controller maintains a temperature within the chamber in a range of −10 to 5 degree Celsius by using a temperature sensor, and a plurality of condensers surrounding the chamber. For example, the temperature is maintained at −2 degree Celsius and the humidity level is maintained at 98% for sterilizing 50 kilograms of tuna in the chamber.

At 608, the gaseous composition is released out of the chamber through at least one outlet (e.g. 118) upon completion of the predefined time period, while introducing at least one of oxygen and atmospheric air through the at least one inlet (e.g. 116) simultaneously, wherein the at least one outlet and the at least one inlet are kept open until presence of the gaseous composition in the atmosphere of the chamber reaches below a threshold value. The oxygen or atmospheric air is obtained from an air purifier unit (e.g. 180). The controller controls a flow rate of the atmospheric air by controlling the aperture of the at least one inlet valve, that is coupled to at least one conduit (e.g. 132) carrying the atmospheric air from the air purifier unit.

The controller opens the at least one outlet and the at least one inlet simultaneously upon completion of the predefined time period to release the gaseous composition from the chamber and introduce atmospheric air into the chamber, until a presence of the gaseous composition in the chamber reaches below a threshold value. The controller detects and monitors a presence of the gaseous composition by using sensors installed within the chamber. For example a carbon monoxide sensor and an ozone sensor may be used to detect presence of CO and ozone within the chamber respectively.

At 610, the one or more samples are procured through an exit of the chamber in an insulated arrangement. The exit is opened by the controller when the gaseous composition is released from the chamber up to the threshold value. In an embodiment, the exit is an airtight sealed door. In an embodiment, the insulated arrangement is a trolley that is insulated with polyurethane foam (PUF), so that the sterilized samples are maintained at the desired temperature post sterilization.

Upon releasing the gaseous composition from the chamber, the one or more samples of the organic product procured from the chamber, is sprayed with a bacteriophages solution. Post spraying the bacteriophages solution, each sample is wrapped in a moisture pad and an antimicrobial paper. In an embodiment, a small portion of the sample is kept visible through the antimicrobial paper and the moisture pad. The wrapped sample is then sealed in at least one of a gas permeable bag and a high barrier bag. In an example, the wrapped sample is zip locked, vacuum-sealed or heat-sealed in the gas permeable bag and the high barrier bag. The high barrier bag is a non-permeable bag (e.g. a nylon bag).

Aforesaid illustrations, described an effective means of sterilizing organic products especially food products at a low temperature viz. −2 degree Celsius. Maintaining a relatively high humidity level during sterilization prevents dehydration of food products that usually occurs at low temperatures. As a result, normal water content is maintained within the organic products during the disclosed sterilization process. The normal water content in sterilized organic products ensures freshness and longer shelf life. Further, use of gaseous chemical agents such as ozone gas and CO gas in the present invention, eliminates the hazards of water retention that occurs within the organic products due to use of aqueous chemical agents for sterilization. Accordingly, there exists no adulteration of weight in the sterilized samples obtained by the present invention.

What is claimed is:

1. A method for sterilizing an organic product in a chamber having a controlled atmosphere, wherein one or more samples of the organic product is placed in the chamber, the method comprising:
   introducing a specified quantity of a gaseous composition comprising a predefined proportion of ozone into the chamber;
   subjecting the one or more samples to the gaseous composition and ultraviolet radiation using at least one ultraviolet tube light, for a predefined time period to sterilize the one or more samples, wherein the one or more samples is accommodated on one or more perforated shelves provided inside the chamber, wherein the at least one ultraviolet tube light is arranged in a manner to radiate an entire surface area of each sample of the organic product accommodated on each perforated shelf, wherein the specified quantity of the gaseous composition further comprises a predefined proportion of carbon monoxide, wherein the carbon monoxide to carbonize the one or more samples of the organic product, and wherein the organic product comprises blood as a constituent; and determining by the controller the specified quantity of the gaseous composition, the predefined proportion of ozone, the predefined proportion of carbon monoxide, and the predefined time period using a model stored in a memory of the controller, wherein a quantity of samples of the organic product, and a type of the organic product provided as an input to the model, wherein the quantity of samples and the type of the organic product is received by the controller via an input interface, and wherein the model comprises operating information of the chamber required for sterilization of a plurality of types and quantities of organic products;

maintaining:
- a humidity level of the atmosphere in the chamber in a range of 90 to 100% by using a humidifier unit and a controller, and
- a temperature within the chamber in a range of −10 to 5 degree Celsius by a plurality of condensers surrounding the chamber;

releasing the gaseous composition out of the chamber upon completion of the predefined time period, while introducing at least one of oxygen and atmospheric air into the chamber, until presence of the gaseous composition in the atmosphere of the chamber reaches below a threshold value, wherein the presence of the gaseous composition is monitored by the controller; and procuring the one or more samples through an exit of the chamber in an insulated arrangement, wherein the exit is opened when the gaseous composition is released from the chamber up to the threshold value.

2. The method of claim 1, wherein the model is built using history data of operating information associated with sterilizing the plurality of types and quantities of the organic products within the chamber.

3. The method of claim 1, wherein subjecting the one or more samples to the gaseous composition further comprises:
circulating the gaseous composition within the chamber by a circulating device installed within the chamber, wherein the circulating device rotates at a predetermined speed based on a control signal provided by the controller.

4. The method of claim 3, wherein post spraying the bacteriophages solution, each sample is wrapped in a moisture pad and an antimicrobial paper prior to sealing in at least one of a gas permeable bag and a nylon bag.

5. The method of claim 1, wherein upon releasing the gaseous composition, the one or more samples of the organic product procured from the chamber, is sprayed with a bacteriophages solution.

6. The method of claim 1, wherein the organic product comprises one or more of fish, meat, vegetables, fruits, roots, seeds, microbes, fungi and blood plasma.

7. A sterilization device comprising:
a chamber having a controlled atmosphere, wherein the chamber is surrounded with a cooling arrangement to maintain a temperature of the chamber in a range of −10 to 5 degree Celsius, wherein the chamber comprises:
an arrangement of shelves to accommodate one or more samples of an organic product;
at least one inlet to permit flow of a gaseous composition comprising a predefined proportion of ozone gas into the chamber; and
at least one outlet through which the gaseous composition is vented out of the chamber upon sterilization of each sample;
a plurality of ultraviolet (UV) tube lights, wherein at least one UV tube light is arranged in one or more of above each shelf and along a top portion of the chamber, wherein an UV tube light emits UV radiation to sterilize at least one of the one or more samples of the organic product; and
a controller to:
control opening and closing of the at least one inlet and the at least one outlet;
determine an operating information required for sterilizing the one or more samples using a model when a quantity of samples of the organic product and a type of the organic product is provided as an input to the model, wherein the input is provided to the model when the one or more samples is introduced into the chamber, wherein the operating information comprises a specified quantity of the gaseous composition, the predefined proportion of the ozone gas, a predefined time period of exposing the one or more samples to the gaseous composition and the UV radiation, a humidity range, a pressure and the temperature of the chamber, and wherein the model comprises operating information associated with sterilizing a plurality types and quantities of organic products within the chamber;
determine a predefined proportion of a Carbon Monoxide (CO) gas to be introduced as a constituent of the gaseous composition through the at least one inlet into the chamber when the organic product contains blood, wherein the controller to determine the predefined proportion of the CO gas using the model;
control the flow rate of the ozone gas by controlling an aperture of one or more inlet valves coupled to one or more first conduits that connect an ozone generator to one or more inlets, wherein the ozone generator provides the ozone gas; and
control the flow rate of the CO gas by controlling an aperture of one or more inlet valves coupled to one or more second conduits that connect a CO generator to one or more inlets, wherein the CO generator provides the CO gas; and
maintain a humidity level of the atmosphere in a range of 90-100% using a humidifier unit, wherein the humidifier unit to provide humidity into the controlled atmosphere based on a control signal received from the controller.

8. The sterilization device of claim 7, wherein the quantity of samples of the organic product and the type of the organic product is received via an input interface coupled to the controller.

9. The sterilization device of claim 7, wherein the controller to:
open the at least one inlet for a first time period to introduce the specified quantity of the gaseous composition into the chamber, wherein the first time period is determined based on a flow rate of the ozone gas, a flow rate of the CO gas and the specified quantity of the gaseous composition;
close the at least one inlet for a predefined time period, upon introduction of the specified quantity of the gaseous composition into the chamber;
switch on one or more of the plurality of ultraviolet tube lights based on a placing of the one or more samples in the chamber for the predefined time period; and
open the at least one outlet and the at least one inlet upon completion of the predefined time period to release the gaseous composition from the chamber through the at least one outlet, and introduce atmospheric air into the chamber through the at least one inlet simultaneously, until a presence of the gaseous composition in the chamber reaches below a threshold value.

10. The sterilization device of claim 9, wherein the controller to:
control a flow rate of the atmospheric air from an air purifier unit into the chamber, by controlling an aperture of one or more inlet valves provided within one or more third conduits, wherein the air purifier unit is connected to one or more inlets of the chamber via the one or more third conduits.

11. The sterilization device of claim 9, wherein the controller to:
build the model using history data comprising the operating information associated with sterilizing the plurality types and quantities of the organic products within the chamber, wherein the history data is stored in a memory coupled to the controller.

12. The sterilization device of claim 7, wherein the chamber further comprises:
an exit that opens upon releasing the gaseous composition up to the threshold value from the chamber, wherein the one or more samples is removed from the chamber in an insulated arrangement through the exit, wherein the exit is an air tight sealed door, and wherein the controller operates the opening of the exit.

13. The sterilization device of claim 7, wherein the chamber further comprises:
a circulating device to circulate the gaseous composition within the chamber at a predefined speed, wherein the predefined speed is based on a control signal provided by the controller.

14. The sterilization device of claim 13, wherein each shelf is arranged at an inclination to facilitate collection of water that condenses on the each shelf into a reservoir placed below the each shelf, wherein the reservoir is connected to one end of the each shelf through a conduit.

15. The sterilization device of claim 7, wherein the arrangement of shelves comprises one or more shelves provided on at least one of one or more inner surfaces of the chamber and on either side of at least one metal frame placed in an inner space of the chamber.

* * * * *